United States Patent [19]

Pederson et al.

[11] Patent Number: 5,391,190
[45] Date of Patent: * Feb. 21, 1995

[54] VARIATION IN CARDIAC CHAMBER VOLUME OR PRESSURE AS A CONTROLLING PARAMETER

[75] Inventors: Brian D. Pederson, St. Paul; Rodney W. Salo, Fridley, both of Minn.

[73] Assignee: Cardiac Pacemakers, Inc., St. Paul, Minn.

[*] Notice: The portion of the term of this patent subsequent to Aug. 11, 2009 has been disclaimed.

[21] Appl. No.: 864,666

[22] Filed: Apr. 7, 1992

Related U.S. Application Data

[63] Continuation of Ser. No. 664,461, Mar. 1, 1991, Pat. No. 5,137,019, which is a continuation of Ser. No. 490,392, Mar. 8, 1990, abandoned.

[51] Int. Cl.⁶ ............................................. A61N 1/362
[52] U.S. Cl. ...................................... 607/23; 607/18
[58] Field of Search ....................................... 607/23, 18

[56] References Cited

U.S. PATENT DOCUMENTS

| | | | |
|---|---|---|---|
| 3,593,718 | 7/1971 | Krasner | 128/419 P |
| 4,566,456 | 1/1986 | Koning et al. | 128/419 PG |
| 4,567,892 | 2/1986 | Plicchi et al. | 128/419 PG |
| 4,576,183 | 3/1986 | Plicchi et al. | 128/723 |
| 4,596,251 | 6/1986 | Plicchi et al. | 128/419 PG |
| 4,686,987 | 8/1987 | Salo et al. | 128/419 PG |
| 4,694,830 | 9/1987 | Lekholm et al. | 128/419 PG |
| 4,702,253 | 10/1987 | Nappholz et al. | 128/419 PG |
| 4,722,342 | 2/1988 | Amundson | 128/419 PG |
| 4,733,667 | 3/1988 | Olive et al. | 128/419 PG |
| 4,773,401 | 9/1988 | Citak et al. | 128/419 PG |
| 4,776,338 | 10/1988 | Lekholm et al. | 128/419 PG |
| 4,790,318 | 12/1988 | Elmquist et al. | 128/419 PG |
| 4,884,576 | 12/1989 | Alt | 128/419 PG |
| 4,901,725 | 2/1990 | Nappholz et al. | 128/419 PG |
| 4,919,136 | 4/1990 | Alt | 128/419 P |

FOREIGN PATENT DOCUMENTS

| | | |
|---|---|---|
| 299208 | 6/1988 | European Pat. Off. . |
| 310024 | 9/1988 | European Pat. Off. . |
| 310025 | 9/1988 | European Pat. Off. . |
| 310026 | 9/1988 | European Pat. Off. . |
| 218007 | 6/1986 | Germany . |

OTHER PUBLICATIONS

"A Cardiac Pacemaker with Activity-Dependent Rate Regulation", H. D. Funke, Jun. 1975, pp. 225–228, Biomedizinische Technik, Band 20.

Primary Examiner—William E. Kamm
Assistant Examiner—Scott M. Getzow
Attorney, Agent, or Firm—Haugen and Nikolai

[57] ABSTRACT

A rate adaptive cardiac pacer is described in which the impedance versus time information derived using impedance plethysmography or the pressure versus time information derived from a pressure transducer in a ventricular chamber is signal processed to recover a modulating envelope due to volume or pressure changes occasioned by respiratory activity. Either or both of the respiratory interval or respiratory depth may be combined in an appropriate rate control algorithm with other parameters also derived from the impedance versus time signal to develop a rate control signal for an implanted pacer.

4 Claims, 2 Drawing Sheets

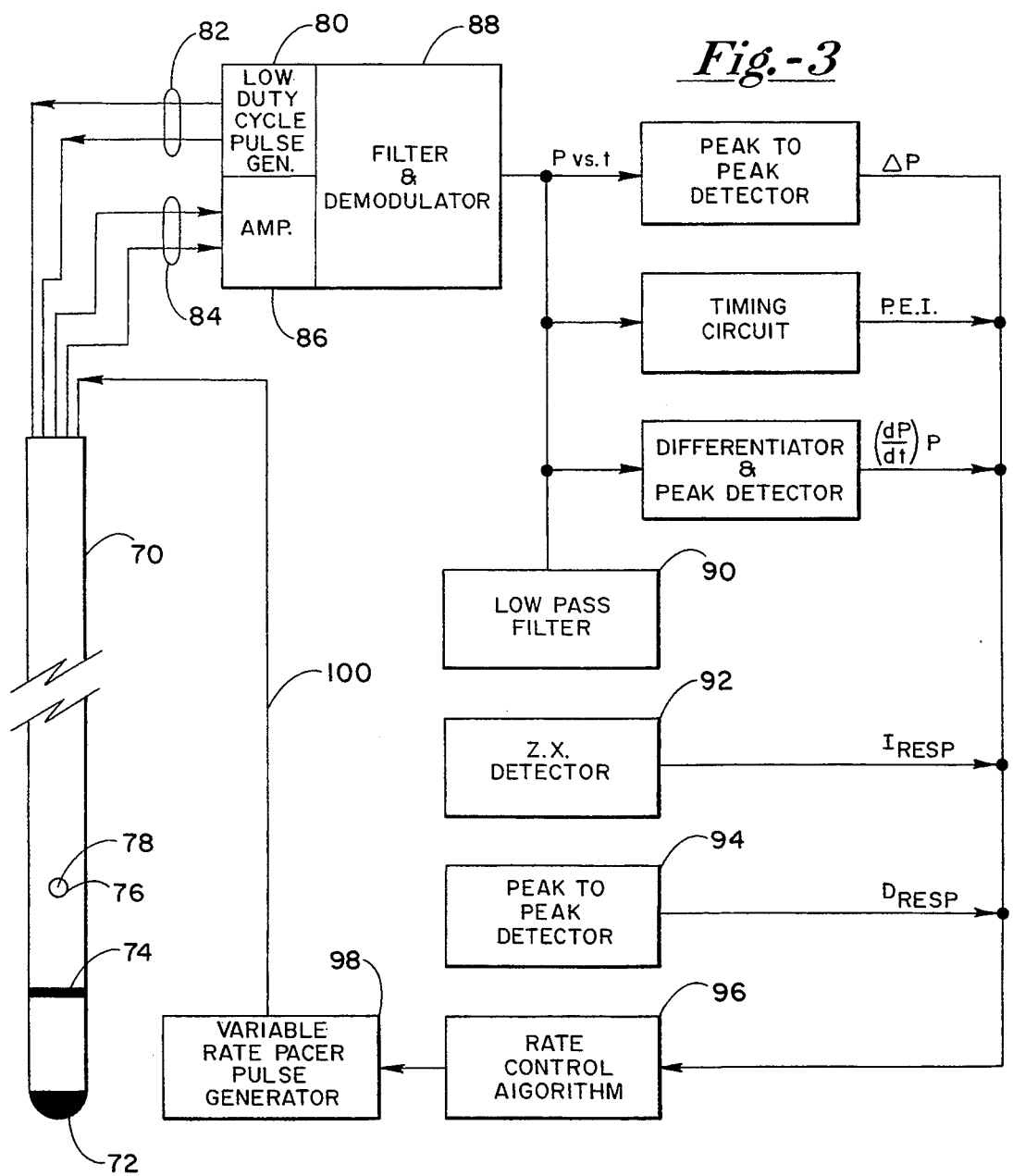

VARIATION IN CARDIAC CHAMBER VOLUME OR PRESSURE AS A CONTROLLING PARAMETER

This is a continuation of application Ser. No. 07/664,461, filed on Mar. 1, 1991, now U.S. Pat. No. 5,137,019, which is a continuation of application Ser. No. 07/490,392, filed on Mar. 8, 1990, now abandoned.

BACKGROUND OF THE INVENTION

I. Field of the Invention

This invention relates generally to a cardiac pacing system in which the pacing rate tracks metabolic need, and more particularly to a rate adaptive pacemaker employing a sensor for detecting variations in cardiac chamber volume or pressure due to respiration and producing a control signal related to the respiration frequency and depth for adjusting the pacing rate relative to a baseline value.

II. Discussion of the Prior Art

Workers in the cardiac pacing field have long recognized the desirability of creating an implantable device capable of maintaining an adequate heartrate in a patient suffering from bradycardia at a nominal level with the individual at rest but which would automatically adapt to changes in metabolic need to increase the pacing rate above that baseline value. One of the earliest attempts at providing such a rate adaptive pacemaker is set forth in the 1977 U.S. Pat. No. 4,009,721 to Mario Alcidi. Alcidi describes a variable rate pacer in which a sensor is provided for measuring blood Ph and developing a control signal proportional to that factor, recognizing that the blood becomes more acidic with exercise. Because of the difficulty in obtaining a reliable sensor which would not drift with time, the Alcidi device never became commercially successful.

The patent literature is replete with rate adaptive pacemaker designs in which a wide variety of physiologic parameters are sensed as an indicator of metabolic need and used to develop a pacing rate control signal for a rate adaptive pacemaker. The following table summarizes several of these approaches:

| INVENTOR | U.S. PAT. NO. | CONDITION SENSED |
| --- | --- | --- |
| Krasner | 3,593,718 | Respiration rate |
| Dahl | 4,140,132 | Physical activity/motion |
| Witzfeld, et al | 4,202,339 | Blood oxygen saturation |
| Rickards | 4,228,803 | QT interval in an ECG waveform |
| Knudson, et al | 4,313,442 | Change in atrial rate |
| Cook, et al | 4,543,954 | Venous blood temperature |
| Koning, et al | 4,566,456 | Right ventricular systolic pressure |
| Plicchi, et al | 4,596,251 | Minute ventilation (respiration) |
| Salo, et al | 4,686,987 | Stroke volume |
| Nappholz, et al | 4,702,253 | Minute volume (respiration) |
| Thornander, et al | 4,712,555 | ECG measured interval |
| Koning, et al | 4,716,887 | Right ventricular blood $pCO_2$ |
| Chirife | 4,719,921 | Pre-ejection period |
| Amundson | 4,722,342 | Multiple difference sensors |
| Koning | 4,730,619 | Ejection time |
| Callaghan | 4,766,900 | Change in depolarization gradient magnitude |
| Citak, et al | 4,773,401 | Pre-ejection interval |
| Elmquist, et al | 4,790,318 | Respiration |
| Lekholm | 4,817,606 | Myoelectrical signals |

The above list is not intended to be exhaustive in that various other workers have received U.S. patents on rate adaptive pacemaker devices and improvements utilizing the sensed parameters set forth in the table and are considered cumulative.

In our earlier U.S. Pat. No. 4,686,987, there is described a rate adaptive cardiac pacer in which means are provided for measuring stroke volume by utilizing an intracardiac impedance waveform and deriving stroke volume-related information from the peak-to-peak swings in the measured impedance waveform. A closer analysis of the intracardiac impedance waveforms reveals amplitude variations due to changes in intrathoracic pressure. In particular, in that atrial and ventricular volumes are affected by factors which influence preload (i.e., the filling of the chamber) and afterload (i.e., the resistance to flow out of the chamber) and that these factors are modulated by the intrathoracic pressure, it becomes possible to monitor variations in intrathoracic pressure by following the low frequency variations in cardiac volume or pressure parameters. For example, the beat-by-beat variation in end-diastolic volume, end-systolic volume, average ventricular volume, or stroke volume or correspondingly, the end-diastolic pressure, end-systolic pressure, average pressure or pulse-pressure may be used as indicators of intrathoracic pressure.

Because the intrathoracic pressure is directly related to respiration (pressure drops during inspiration and increases during expiration), the amplitude of the variation in intrathoracic pressure during a respiratory cycle is directly related to the depth of respiration.

SUMMARY OF THE INVENTION

In accordance with the present invention, there is provided an impedance system for measurement of right ventricular (or atrial) volume or a pressure transducer for measurement of right ventricular (or atrial) pressure, a signal processing means to extract one of the volume or pressure parameters on a beat-by-beat basis to thereby yield a signal varying at the respiratory rate and with a peak-to-peak amplitude proportional to respiratory depth. Further signal processing means are provided to extract the period of the respiratory signal and its peak-to-peak amplitude and the resulting signals are utilized by an algorithm to contribute to establishing the desired pacing rate for an implanted rate adaptive pulse generator.

While it is recognized that other workers in the field have utilized respiration rate as an indicator of metabolic demand and have used that rate signal to adjust the pacing rate of a pulse generator, we believe we are the first to recognize that the right ventricular volume, as measured by intracardiac impedance, is directly influenced by intrathoracic volume and pressure and have quantified these influences and processed them in developing a control signal for a rate adaptive pacer. That is to say, previous devices relying upon respiration as a pacing rate adjusting parameter have measured variations in thoracic impedance, either measured with electrodes across the chest or between electrodes within a great vessel and a pacemaker can. In our invention, we sense actual volume or pressure variations within the right ventricular (or atrial) chamber due to respiration and derive an independent control parameter from the very same leads used to sense changes in stroke volume. Thus, by monitoring the lower frequency changes in ventricular volume, i.e., those associated with breathing, and using this information in addition to other parameters derived using the same hardware components to control pacing rate, a more precise control over pacing rate based upon metabolic need or demand is achieved.

It is thus a primary object of the invention to provide an improved pacemaker having means for deriving from an intracardiac impedance waveform information relating to frequency and depth of respiration and developing a control signal therefrom which, when applied to a rate adaptive pacemaker, causes the pulse rate to track metabolic need.

It is another object of the invention to provide a pacemaker having means for developing multiple rate controlling signals which can be combined in an appropriate algorithm to produce a rate control signal which more accurately and reliably modifies the pacing rate to match the instantaneous metabolic needs of the patient.

BRIEF DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 3 is a system block diagram of a rate adaptive pacer constructed in accordance with a second embodiment of the present invention.

DESCRIPTION OF THE PREFERRED EMBODIMENT

Figure 1:
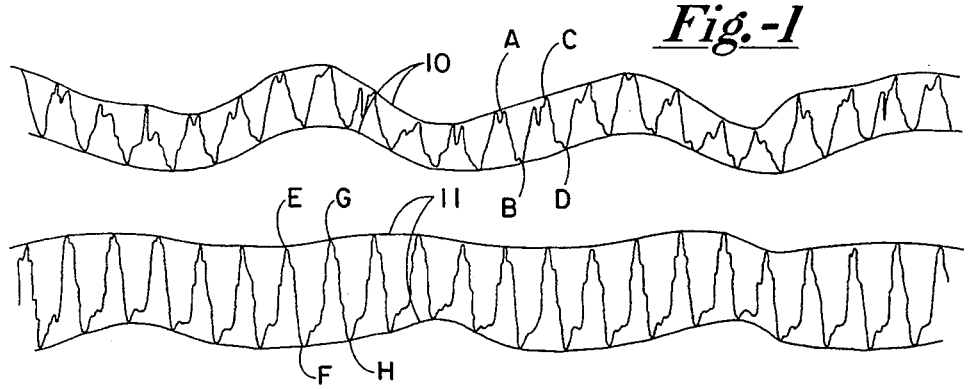
FIG. 1 is a plot of the variation of right ventricular volume and right ventricular pressure on a beat-by-beat basis.

Referring to the waveforms of FIG. 1, in the uppermost plot there is shown the variation in right ventricular volume as measured when using an impedance plethysmography technique, such as is disclosed in Salo et al U.S. Pat. No. 4,686,987. The individual excursions labeled A, B, C, D are due to the beating action of the heart whereas the lower frequency modulating wave or envelope identified by numeral 10 is determined to be a respiration-related variation in the right ventricular volume measurement due to changes in intrathoracic pressure during respiration. It is found that as the diaphragm moves down to draw air into the lungs, the right ventricular volume increases whereas when expiration takes place, the right ventricular volume decreases.

The lowermost plot in FIG. 1 shows the variation in pressure within the right ventricle measured using a sensitive, solid-state pressure transducer located near the distal end of an endocardial lead. The individual excursions, such as labeled E, F, G, H, are due to normal systolic and diastolic pressure variations while low frequency variations represented by the line 11 has been determined to be due to pressure variations in the ventricular chamber due to intrathoracic pressure changes attendant to respiration.

The present invention makes use of this fact in creating a control signal for a rate adaptive pacemaker. More particularly, and with reference to a first embodiment illustrated by the block diagram of FIG. 2, there is identified by numeral 10 a set of conductors which extend through a suitable catheter or lead 12 into the right ventricle of the heart. As in our earlier U.S. Pat. No. 4,686,987, electrical conductors 14 and 16 couple the output of a carrier oscillator circuit 18 to the drive electrodes 20 and 22 mounted on the surface of the catheter 12. The drive electrode 20 may be on the catheter or may be on the pulse generator can. Disposed between the drive electrodes are a pair of sense electrodes 24 and 26 which are coupled by conductors 28 and 30 to the inputs of a sensing amplifier 35. The output of the sense amplifier is delivered to impedance processing circuit 36 which includes amplifying, filtering and demodulating circuitry as in our earlier referenced U.S. Pat. No. 4,686,987.

When the catheter 12 is disposed with its tip at the apex of the heart's right ventricle and an alternating current pulsatile signal of low duty cycle from the high frequency oscillator 18 is impressed across the drive electrodes 20 and 22, that high frequency signal will be modulated by the changes in impedance of the blood between electrodes 24 and 26. By utilizing a pulsatile AC signal of low duty cycle, battery power is conserved.

The signal appearing at the output point 38 from the impedance processing circuit 36 is a time-varying signal corresponding to the impedance measured within the heart. When the Z vs. t signal is applied to a peak to peak detector as at 40, the resulting signal at the output of that peak to peak detector is proportional to the stroke volume of the heart. This stroke volume signal is present on line 42.

Next, with reference to the Citak et al U.S. Pat. No. 4,773,401 assigned to applicant's assignee, the impedance waveform present at point 38 may also be signal processed by an appropriate timing circuit, as at 44, to develop at its output 46 a time interval-related signal proportional to the period between the occurrence of a paced electrical event or a spontaneous QRS complex and ending with the point where the Z vs. t signal reaches a predetermined threshold. As pointed out in Citak et al, this signal may be used to adjust the rate of a rate adaptive pacemaker.

Next, referring to the Olive et al U.S. Pat. No. 4,733,667 also assigned to applicant's assignee, the Z vs. t signal appearing at junction 38 may be applied via a differentiator and peak detector circuit, as at 48, to produce an output signal on line 50 proportional to the peak value of the derivative of the impedance vs. time waveform. It has been found that by using the average peak value of the first derivative of the impedance waveform as the control signal to be used in modifying the timing cycle of a rate adaptive pacer, problems due to positional changes of the patient can be obviated.

In accordance with the first embodiment of the present invention, we now take the Z vs. t signal present at junction 38 and apply it to a low pass filter 52 to effectively recover the modulating envelope identified by trace 10 in FIG. 1 and then apply that signal to a zero-crossing detector 54 to create a signal on line 56 relating to the respiration interval $I_{RESP}$. This respiration interval is inversely related to respiration rate. The same signal from the low pass filter 52 may then be applied to a peak to peak (or minimum to maximum) detector as at 58 which is effective to produce a further signal on line 60 proportional to the respiration depth, $D_{RESP}$.

Some or all of the signals SV, PEI, (dZ/dt)P, $I_{RESP}$ and $D_{RESP}$ may then be utilized in a rate control algorithm 62 to develop a rate control signal on line 64 which, when applied to the timing circuit of a variable rate pacer pulse generator 66 will cause the rate thereof to track metabolic need with the stimulating output signal being applied via a conductor 32 in the catheter 12 to the stimulating tip electrode 22 positioned in the apex of the right ventricle.

As indicated above, at this point, there are five parameters available for use in the rate control algorithm. Recognizing that it is possible to examine the signals represented on lines 42, 46, 50, 56 and 60 so as to determine which parameters should be excluded in modifying the pacing rate, only the most reliable parameters need be selected and employed. As an example, if the Z vs. t signal is rich in random noise, the (dZ/dt)P signal becomes unreliable and less useful. Also, if the Z vs. t waveform is distorted during the ejection phase, which may happen due to movement or motion of the lead 12 within the right ventricle, the pick-off point for the pre-ejection interval may be adversely affected and this interval is to be down-played in its overall effect on the characteristics of the rate control signal on line 64.

A possible rate control algorithm may be expressed as follows:

$$\text{pacing interval} = a^*(SV - SV_{BASE}) + b^*(PEI - PEI_{BASE}) + c^*(dZ/dt - dZ/dt_{BASE}) + d^*(I_{RESP} - I_{RESP}^{BASE}) + e^*(D_{RESP} - D_{RESP}^{BASE})$$

where a, b, c, d, e are constants (either predetermined or programmable).

Another possibility for a rate control algorithm is:

$$\Delta(\text{pacing interval}) = a^*(SV - SV_{base}) + b^*(PEI - PEI_{base}) + c^*(dZ/dt - dZ/dt_{base}) + d^*(D_{RESP}/I_{RESP} - D_{RESP}^{BASE}/I_{RESP}^{BASE})$$

The base values set out in the equations may either be determined at the time of implant or at a time of later follow-up with the patient and will normally relate to conditions when the patient is at rest. It is also contemplated that the base values referred to may be updated automatically in a microprocessor based implantable, rate-adaptive pacer by computing a long-term (several hours) average of the parameter in question. Any one of the five indicated parameters (stroke volume, pre-ejection interval, rate of change of impedance with time, respiration interval and respiration depth) may be down-played or even ignored by setting its coefficient (a, b, c, d, e) low or equal to zero, respectively.

The approach provided by the present invention is advantageous over prior art arrangements because it permits one to average a response over a plurality of sensors, thereby minimizing the effect of an error in any one of them. More importantly, all of the parameters are derived from the same basic signal (Z vs. t), allowing a single endocardial lead for sensing and pacing and only a modest increase in circuitry employed in the implantable pacer module.

It should also be recognized that if the rate control algorithm employed only involves respiration-related information, it offers an advantage over the prior art minute volume algorithm of the Nappholz U.S. Pat. No. 4,702,253 in that our algorithm allows the response to be better tailored to the patient's physical capabilities. For example, consider the use of the algorithm:

$$\text{new pacing interval} = \text{current pacing interval} - a^*(I_{RESP} - I_{RESP}^{BASE}) - b^*(D_{RESP} - D_{RESP}^{BASE})$$

When dealing with an untrained person, i.e., one not involved in an on-going exercise regimen, the respiration interval will change very rapidly with a relatively small change in depth. In this case, the rate change response of the pacer can be slowed by using a small value for the constant "a" or, alternatively, it can be exaggerated with a large "a" value without effecting the response to respiratory depth changes. Thus, factors such as initial response speed and speed of recovery can be adjusted while maintaining a simple linear algorithm.

Referring next to FIG. 3, there is shown a second or alternative embodiment of the present invention. The embodiment of FIG. 3 is very much like that of FIG. 2 except that, rather than measuring the volume changes of the right ventricular chamber due to intrathoracic pressure variations, the embodiment of FIG. 3 directly measures the pressure variations within the right ventricle using a sensitive, catheter-mounted solid-state pressure transducer. More particularly, the pacer lead assembly 70 may include a conventional tip electrode 72 and a bipolar ring electrode 74 for both stimulating cardiac tissue and for sensing cardiac activity within the right ventricle. Alternatively, a monopolar lead may be used which would include only a stimulated tip electrode with the return or indifferent electrode being the metal case of the pacemaker housing, all as is well known in the art.

The lead 70 further includes a window opening 76 passing through the wall of the tubular sheath and disposed within the lumen of the tubular sheath comprising the catheter 70 is a solid-state pressure transducer of the type typically including a body, means for converting pressure signals to electronic signals (e.g. piezo resistors on a chemically etched silicon diaphragm), means for interfacing the transducer with external signal processing circuitry. A commercially available transducer which may be utilized in the catheter 70 is the "OEMeds" (tm) sensor manufactured by the Cardiovascular Products Division of Gould Incorporated of Oxnard, Calif. That device is deemed to be exemplary only and it is to be understood that other microminiature solid-state pressure transducers that will work in the system of the present invention are also commercially available.

A compliant membrane 78 is inserted in the window and it is through this compliant membrane that pressure waves to be monitored reach the transducer. The membrane, of course, serves to exclude body fluids from the interior of the catheter body and especially the piezo resistive elements comprising the transducer.

The solid state pressure transducer is configured in a Wheatstone bridge arrangement and is driven by a low duty cycle pulsatile alternating current energization from a pulse generator 80 over lines 82 and the output therefrom is applied via conductors 84 to a signal amplifying circuit 86. The output from the amplifier 86 will be a modulated carrier signal where the modulation contains information relating to pressure changes to which the pressure transducer has been subjected. Thus, when the tip electrode 72 of the catheter is placed at the apex of the right ventricle, the window 76 will be located within the right ventricle and, hence, the transducer will be subjected to pressure variations occurring within that heart chamber. The output from the amplifier 86 is then applied to a filter and demodulator circuit 88 which functions to extract the modulation envelope and remove the carrier.

The output from the filter demodulator circuit 88 thus comprises a pressure vs. time (p vs. t) signal having the waveform of the type shown in the lowermost trace in FIG. 1. By passing that signal through a further low pass filter 90 whose cutoff frequency is set to exclude the signal component due to systolic and diastolic pressure variations or by passing the signal through a positive or negative peak detector, the component represented by waveform 11 in FIG. 1 results. As mentioned, that waveform corresponds to intracardiac-pressure variations, variations in average pressure, end diastolic or end-systolic pressure, $\Delta P$, due to intrathoracic pressure changes accompanying respiration.

Figure 2:
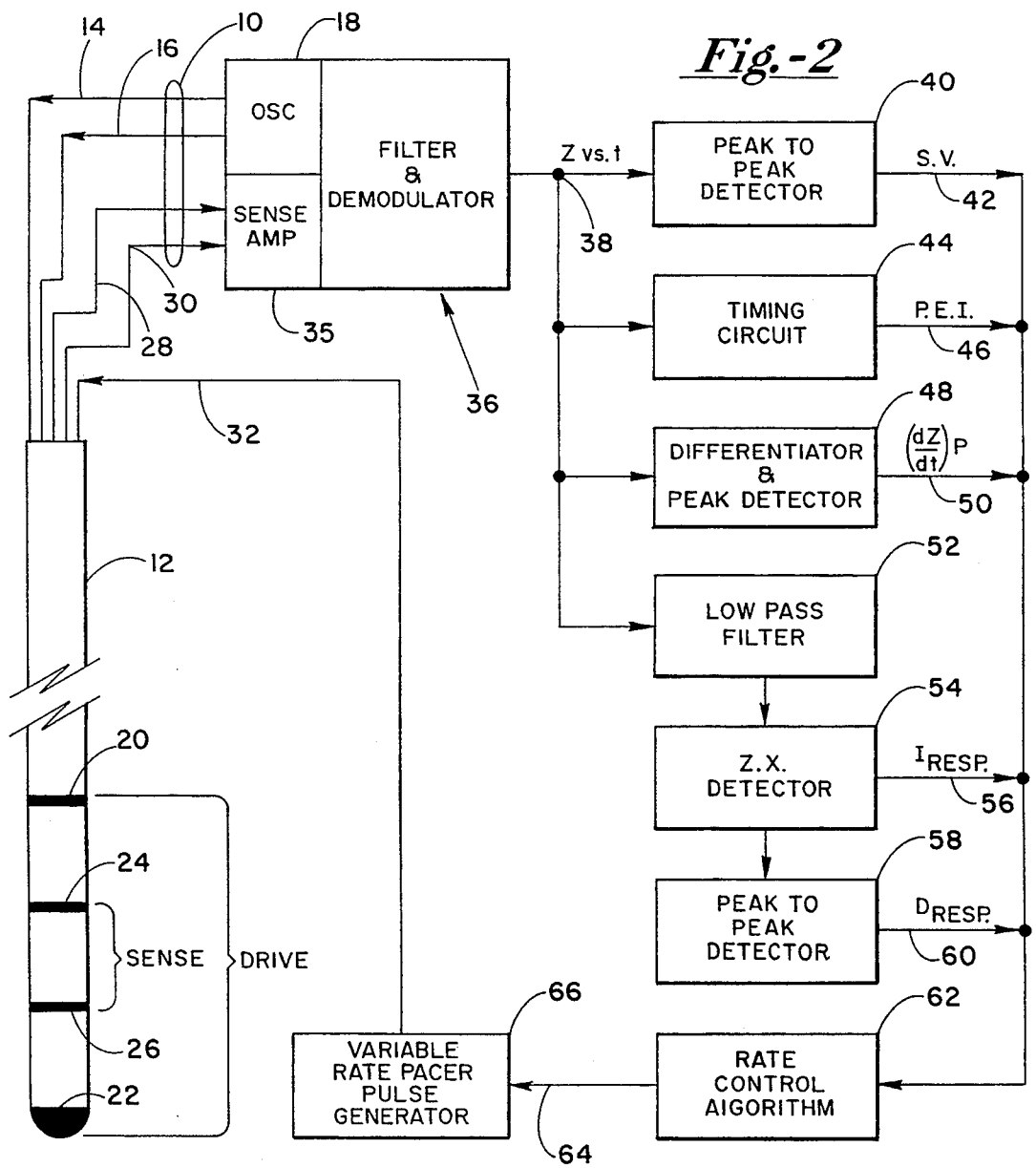
FIG. 2 is a system block diagram of a rate adaptive pacer constructed in accordance with a first embodiment of the present invention.

By applying the signal output from the low pass filter 90 to an appropriate level-crossing detector 92, it is possible to derive a value related to the respiratory interval in the same way that the zero-crossing detector in the embodiment of FIG. 2 operates on the volume variations. Moreover, the output from the level crossing detector can also be applied to a peak detector 94 for creating an output signal therefrom related to the depth of respiration. As in the embodiment of FIG. 2, one or both of these signals may be used in an appropriate rate control algorithm (box 96) to create a control signal effective to vary the rate at which the variable rate pacer pulse generator 98 produces output cardiac stimulating pulses on line 100 leading to the stimulating tip electrode 72.

Those skilled in the art will recognize that the system reflected by the block diagrams of FIGS. 2 and 3 may be implemented using all analog circuitry or, alternatively, by incorporating an analog-to-digital converter at the output of the filter & demodulator circuit 36, the circuits downstream from such an A/D converter can readily be implemented in a programmed microprocessor or microcontroller architecture.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

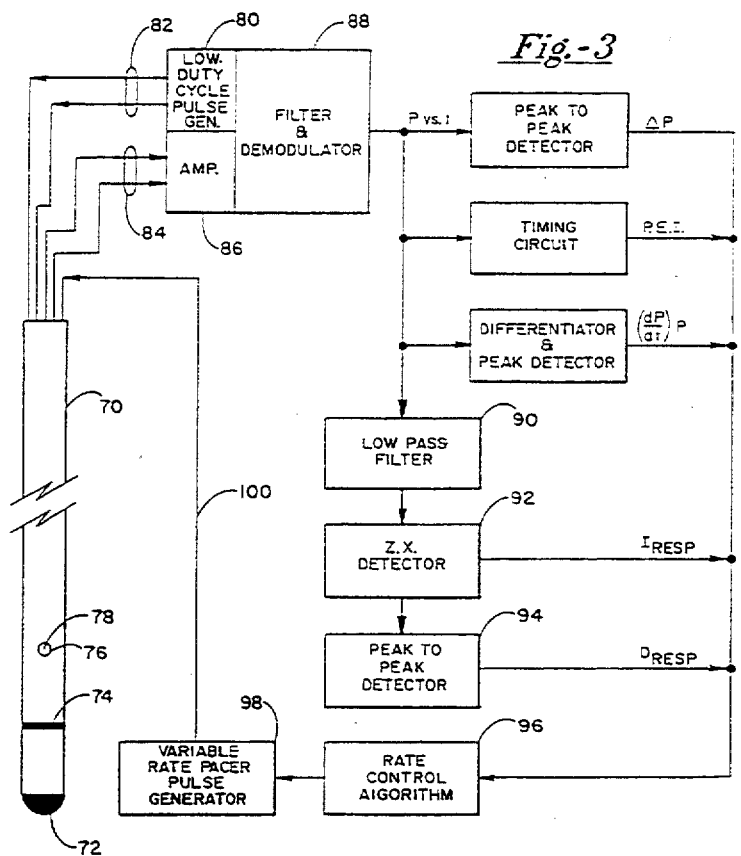

What is claimed is:

1. A rate adaptive pacer comprising:

implantable pulse generator means for normally producing cardiac stimulating pulses at a predetermined lower rate;

sensing means for sensing impedance in the blood in a selected cardiac chamber;

means for producing a time varying impedance signal proportional to the intracardiac impedance sensed in the selected cardiac chamber due to the beating action of the heart;

means for extracting from the time varying impedance signal a modulation signal due to volume changes;

means for relating the modulation signal to the respiratory activity of the patient and processing the modulation signal to extract quantitative information therefrom with respect to the respiratory activity of the patient in whom the pulse generator means is implanted, the respiratory activity information including that relating both to the respiration interval ($I_{RESP}$) and the respiration depth ($D_{RESP}$) wherein the means for relating the modulation signal to $I_{RESP}$ comprises a zero-crossing detector and wherein the means for relating the modulation signal to $D_{RESP}$ comprises a peak to peak amplitude detector; and means for producing a rate control signal from the processed modulation signal which, when applied to the pulse generator means, changes the rate at which the stimulating pulses are produced from the predetermined lower rate to a higher rate in accordance with a known relationship between $I_{RESP}$ and $D_{RESP}$ expressed as an empirical algebraic function.

2. A rate adaptive pacer comprising:

implantable pulse generator means for normally producing cardiac stimulating pulses at a predetermined lower rate;

sensor means for sensing the pressure in a selected cardiac chamber;

means for producing a time varying signal proportional to the pressure sensed in the selected cardiac chamber due to the beating action of the heart;

means for extracting from the time varying pressure signal a modulation signal due to pressure changes;

means for relating the modulation signal to the respiratory activity of the patient and extracting quantitative information therefrom relating to the respiratory activity of the patient in whom the pulse generator means is implanted, the respiratory activity information including that related to the respiration interval ($I_{RESP}$) and the respiration depth ($D_{RESP}$); and means for producing a rate control signal from the modulation signal which, when applied to the pulse generator means, changes the rate at which said stimulating pulses are produced from said predetermined lower rate to a higher rate in accordance with a known relationship between $I_{RESP}$ and $D_{RESP}$ expressed as an empirical algebraic function.

3. A method for controlling a rate adaptive pacer comprising an implantable pulse generator means for normally producing cardiac stimulating pulses at a predetermined lower rate comprising the steps of:

sensing an intracardiac parameter selected from the group consisting of impedance and pressure in the blood in a selected cardiac chamber;

producing a time varying signal related to the magnitude of the intracardiac parameter sensed in the selected cardiac chamber due to the beating action of the heart;

extracting from the time varying signal from the sensed parameter a modulation signal due to the selected one of impedance volume changes or pressure changes;

relating the modulation signal to and extracting quantitative information from the modulation signal with respect to the respiratory activity of the patient in whom the pulse generator means is implanted, the respiratory activity information including that relating both to the respiration interval ($I_{RESP}$) and the respiration depth ($D_{RESP}$) wherein the modulation signal is related to $I_{RESP}$ by subjecting it to a zero-crossing detector and wherein the modulation signal is related to $D_{RESP}$ by processing it utilizing a peak to peak amplitude detector;

producing a rate control signal from the modulation signal which, when applied to the pulse generator means, changes the rate at which the stimulating pulses are produced from the predetermined lower rate to a higher rate in accordance with a known relationship among the selected parameter, $I_{RESP}$ and $D_{RESP}$ in which the modulation signal is used to generate the rate control signal to control the interval between the cardiac stimulating pulses according to an empirical algebraic relationship; and applying the rate control signal to the pulse generator.

4. The method of claim 3 wherein the selected parameter is impedance.

* * * * *

UNITED STATES PATENT AND TRADEMARK OFFICE
CERTIFICATE OF CORRECTION

PATENT NO. : 5,391,190            Page 1 of 2

DATED       : February 14, 1995

INVENTOR(S) : Pederson, et al.

It is certified that error appears in the above-indentified patent and that said Letters Patent is hereby corrected as shown below:

<u>In the Drawings:</u>
Please replace Figure 3 with the attached Fig. 3 as shown on the attached page.

Signed and Sealed this

Twenty-fifth Day of July, 1995

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,391,190
DATED : February 14, 1995
INVENTOR(S) : Pederson, et al.

It is certified that error appears in the above-indentified patent and that said Letters Patent is hereby corrected as shown below: